United States Patent
Lin et al.

[11] Patent Number: 6,140,546
[45] Date of Patent: Oct. 31, 2000

[54] HYDROCARBON DEHYDROCYCLIZATION PROCESS

[75] Inventors: Fan-Nan Lin, Bartlesville, Okla.; Brian H. Limoges; Peter C. Stynes, both of Borger, Tex.

[73] Assignee: Phillips Petroleum Company, Bartlesville, Okla.

[21] Appl. No.: 09/326,811

[22] Filed: Jun. 4, 1999

[51] Int. Cl.[7] .............................. C07C 15/00; C07C 2/52; C07C 6/00; C10G 35/06; C10G 35/00
[52] U.S. Cl. .................... 585/419; 585/407; 585/413; 208/139; 208/141
[58] Field of Search .................. 208/139, 141; 585/414, 413, 407

[56] References Cited

U.S. PATENT DOCUMENTS

| | | |
|---|---|---|
| 3,158,662 | 11/1964 | Reichle et al. ............... 260/683.75 |
| 3,907,705 | 9/1975 | Mertzweiller et al. ............ 252/430 |
| 4,220,521 | 9/1980 | Antos ........................ 208/139 |
| 5,043,002 | 8/1991 | Dobbins et al. ................ 65/3.12 |
| 5,160,032 | 11/1992 | Holmgren et al. .............. 208/46 |
| 5,414,184 | 5/1995 | Wu et al. .................... 585/708 |

*Primary Examiner*—Marian C. Knode
*Assistant Examiner*—Thuan D. Dang
*Attorney, Agent, or Firm*—Richmond, Hitchcock, Fish & Dollar

[57] ABSTRACT

In a process for the dehydrocyclization of a dehydrocyclizable hydrocarbon contained in a dehydrocyclization feed stream which comprises contacting said dehydrocyclizable hydrocarbon in a dehydrocyclization zone under dehydrocyclization conditions in the presence of a dehydrocyclization catalyst, the improvement comprises carrying out said dehydrocyclization process in the presence of a metal chloride additive in said dehydrocyclization feed stream, said metal chloride additive being present in an amount sufficient to inhibit deactivation of such dehydrocyclization catalyst.

12 Claims, No Drawings

HYDROCARBON DEHYDROCYCLIZATION PROCESS

The invention relates to a dehydrocyclization process. In one aspect the invention relates to the stabilization of RON values in a dehydrocyclization process. In another aspect this invention relates to the stabilization of BTX values in a dehydrocyclization process. A still further aspect of this invention relates to the prolonging of catalyst life in a dehydrocyclization process.

The dehydrocyclization of dehydrocyclizable hydrocarbons is an important commercial process because of the great and expanding demand for aromatic hydrocarbons for use in the manufacture of various chemical products as well as for the production of high octane gasolines as is well known to those skilled in the art.

The demand for aromatics such as benzene by the petrochemical industry as well as the need for toluene and xylene products has led to an ever increasing demand for such products.

Responsive to this demand for these aromatic products, the art has developed a number of alternative methods to produce them in commercial quantities. One method that has been widely studied involves the selective dehydrocyclization of a dehydrocyclizable hydrocarbon by contacting the hydrocarbon with a suitable catalyst at dehydrocyclization conditions. As is the case with most catalytic procedures, the principal measure of effectiveness for this dehydrocyclization method involves the ability to perform its intended function with minimum interference of said reactions for extended periods of time. The analytical terms used in the art to broadly measure how well a particular catalyst performs its intended function in a particular hydrocarbon conversion reaction are activity, selectivity and stability. These terms are generally defined for a given reactant as follows. Activity is a measure of the catalyst's ability to convert the hydrocarbon reactant into products at a specified severity level where severity level means the specific reaction conditions used— that is the temperature, pressure, contact time and presence of diluents such as hydrogen. Selectivity usually refers to the amount of desired product or products obtained relative to the amount of the reactant charged or converted. Stability refers to the rate of change with time of the activity and selectivity parameters—obviously the smaller rate implying the more stable catalyst. More specifically, in a dehydrocyclization process, activity commonly refers to the amount of conversion that takes place for a given dehydrocyclizable hydrocarbon at a specified severity level and is typically measured on the basis of disappearance of the dehydrocyclizable hydrocarbon. Selectivity is typically measured by the amount, calculated on a weight percent of feed basis or on a mole percent of converted dehydrocyclizable hydrocarbon basis, of the desired aromatic hydrocarbon or hydrocarbons obtained at the particular activity or severity level. Stability is typically equated to the rate of change with time of activity as measured by disappearance of the dehydrocyclizable hydrocarbon and of selectivity as measured by the amount of desired aromatic hydrocarbon produced. Accordingly, a major problem facing workers in the hydrocarbon dehydrocyclization ring-closure art is the development of a more active and selective system that has good stability characteristics.

Numerous systems have been developed to effect the dehydrocyclization of hydrocarbon feeds. One such well known system is that which employs a platinum group metal on a porous support such as platinum on alumina. While such systems have been found to be very attractive in the production of aromatics such as benzene, toluene and xylene, there is still encountered the problem of catalyst deactivation. There are believed to be a number of causes of catalyst deactivation. One such cause of catalyst deactivation is the formation and accumulation of high molecular weight hydrocarbons such as coke within the pores of the dehydrocyclization catalyst as well as on the surface of the catalyst. The formation and accumulation of such compounds causes a high rate of catalyst deactivation, and thus a shorter run life of the catalyst as well as an unsteady yield of desired aromatic hydrocarbon product.

In addition, when carrying out commercial processes for the dehydrocyclization of hydrocarbons such as n-heptane there is also experienced erratic fluctuations in the benzene, toluene, xylene (BTX) yield and gradual decrease in the octane (RON) values with time on stream.

In addition, impurities present in the dehydrocyclization feed stream contribute to a rapid decrease in catalyst activity. Pretreatment of the dehydrocyclization feed stream prior to dehydrocyclization to remove a major portion of these impurities is one option to help alleviate catalyst deactivation, but this route is expensive because additional equipment and operating costs are required. Also, the levels of these impurities in the dehydrocyclization feed stream may fluctuate and pretreatment of the dehydrocyclization feed stream may not always be adequate.

SUMMARY OF THE INVENTION

It is thus an object of this invention to carry out the dehydrocyclization of a dehydrocyclization feed stream comprising a suitable paraffinic hydrocarbon and hydrogen in the presence of a dehydrocyclization catalyst such as a platinum group metal on a porous support in the presence of a dehydrocyclization feed stream additive which is effective to alleviate or diminish the deactivation of such catalysts.

Another object of this invention is to provide a dehydrocyclization process wherein there is achieved a stabilization of RON and BTX values.

Another object of this invention is to provide a method by which the activity or run life of a dehydrocyclization catalyst can be enhanced or essentially prolonged resulting in a substantially constant conversion, i.e., aromatization, of hydrocarbon.

A still further object of this invention is to provide a method which permits the economical dehydrocyclization of alkanes such as n-heptane to BTX while achieving an exceptionally long and useful operating life for the associated dehydrocyclization catalyst while also achieving an enhanced RON value for the product.

The present invention, directed to a more effective method of alleviating or diminishing catalyst deactivation problems while securing a stable BTX and RON value for the process products is based upon our discovery that by the addition of certain additives as hereinafter defined to the dehydrocyclization feed stream there is counteracted such catalyst deactivation and erratic performance. The amount of additive used is important in alleviating or diminishing catalyst deactivating effects and in achieving a system which avoids erratic fluctuation in BTX yield and RON decrease over time on stream.

The dehydrocyclization process of this invention is based upon the carrying out of the dehydrocyclization of a dehydrocyclizable hydrocarbon in a dehydrocyclization feed stream in a dehydrocyclization zone in the presence of a dehydrocyclization catalyst and in the presence of an additive, comprising at least one added metal halide, in such dehydrocyclization feed stream. Such additive is present in an amount sufficient to alleviate or diminish the deactivation of the dehydrocyclization catalyst and to maintain a substantially constant conversion, i.e., dehydrocyclization, of at least one dehydrocyclizable hydrocarbon to at least one aromatic product at effective dehydrocyclization conditions.

The process of the present invention provides several benefits to the art such as (1) extending the run life of the catalyst which translates into longer operating runs between catalyst regeneration; (2) the ability to operate the process with fewer catalyst regeneration cycles which translates into safer operation, less downtime, and great economic benefit; (3) the usual erratic fluctuations in BTX are avoided; (4) the usual gradual decrease in RON value of the product with time on stream is avoided; and (5) there is achieved a totally unexpected increase in the RON values of product over time on stream.

Other aspects, objects and the several advantages of the invention will be apparent from the following specification and appended claims.

DETAILED DESCRIPTION OF THE INVENTION

The present invention is based upon my discovery that in a process for the dehydrocyclization of a dehydrocyclizable hydrocarbon in a dehydrocyclization feed stream wherein such dehydrocyclizable hydrocarbon is contacted in a dehydrocyclization zone under dehydrocyclization conditions in the presence of a dehydrocyclization catalyst, that the addition of from 0.01 to about 10.0 ppb (parts per billion parts of feed) of metal chloride compound to the dehydrocyclization feed stream will result in not only the prolonging of the life of the dehydrocyclization catalyst but, in addition, there is achieved a stability in the BTX production and octane numbers for the resulting aromatized products.

The term "metal chloride compound" as employed herein is intended to mean a chloride of a Group IIIA or Group V. The elements of Group IIIA are aluminum, boron, gallium, indium and thallium and the elements of Group V are phosphorous, arsenic, antimony and bismuth.

The subject invention is broadly an improved method for dehydrocyclizing a dehydrocyclizable hydrocarbon to produce an aromatic hydrocarbon. In a narrower aspect, the present invention involves a method of dehydrocyclizing aliphatic hydrocarbons containing 6 to 20 carbon atoms per molecule to monocyclic aromatic hydrocarbons with minimum production of side products such as $C_1$ to $C_5$ hydrocarbons, bicyclic aromatics, olefins and coke.

Regarding the dehydrocyclizable hydrocarbon that is subjected to the improved process of this invention, it can be in general any aliphatic hydrocarbon or substituted aliphatic hydrocarbon capable of undergoing ring-closure to produce aromatic hydrocarbons. More particularly, suitable dehydrocyclizable hydrocarbons are aliphatic hydrocarbons containing 6 to 20 carbon atoms per molecule such as $C_6$ to $C_{20}$ paraffins. Suitable examples of dehydrocyclizable hydrocarbons are paraffins such an n-hexane, 2-methylpentane, 3-methylpentane, n-heptane, n-octane, n-nonane, n-decane and the like compounds.

In a presently preferred embodiment of this invention, the dehydrocyclizable hydrocarbon is a paraffin hydrocarbon having about 6 to 10 carbon atoms per molecule.

The term "dehydrocyclization feed stream" refers to any feed stream containing a dehydrocyclizable hydrocarbon as described herein. An example of a suitable dehydrocyclization feed stream includes, but is not limited to, a naphtha fraction boiling in the range of about 122° F. to about 450° F., preferably boiling in the range of about 150° F. to about 400° F.

The catalyst employed in the process of the present invention comprises platinum and a support material including, but not limited to, alumina, chlorinated alumina, silica, titania, zirconia, aluminosilicates, zinc alumina, zinc titanate, zeolite and mixtures thereof. A presently preferred catalyst comprises platinum on alumina. Generally, the concentration of platinum in the catalyst is in the range of from about 0.01 weight percent of the catalyst to about 10 weight percent of the catalyst.

The catalyst used in the present invention for the dehydrocyclization of a feed hydrocarbon comprises a porous carrier material having combined therewith catalytically effective amounts of a platinum group component.

The porous carrier material utilized is preferably one that is a porous adsorptive, high surface area support having a surface area of about 25 to 500 m$^2$/g. The porous carrier material should be relatively refractory to the conditions utilized in the hydrocarbon conversion process and it is intended to include within the scope of the present invention carrier materials which have traditionally been utilized in dual-function hydrocarbon conversion catalysts. In one embodiment of this invention, the presently preferred porous carrier materials for use in the present invention are refractory inorganic oxides. Most preferred are the alumina compounds such as the crystalline aluminas known as gamma, eta and theta alumina. Such alumina carrier materials may be prepared in any suitable manner and may be synthetically prepared or natural occurring. Whatever type of alumina is employed, it may be activated prior to use by one or more treatments including drying, calcination, steaming and it may be in a form known as activated alumina, activated alumina of commerce, porous alumina or alumina gel.

An essential ingredient of the dehydrocyclization catalyst is the platinum group component. Such a group includes the use of platinum, iridium, osmium, ruthenium, rhodium, palladium or mixtures thereof. Such platinum group component should be uniformly dispersed throughout the porous carrier material in the elemental metallic state. Generally, the amount of platinum group in the catalyst is an amount of about 0.01 to about 2 weight percent of final catalytic composition.

The platinum group component may be incorporated in the porous carrier material in any suitable manner known to result in a relatively uniform distribution of this component in the carrier material such as coprecipitation or cogelation, ion-exchange or impregnation.

The utilization of a platinum group chloride compounds such as chloroplatinic, chloroiridic, or chloropalladic acid is preferred since it facilitates the incorporation of both the platinum group component and at least a minor quantity of halogen component in a single step.

Hydrogen chloride or the like acid is also generally added to the impregnation solution in order to further facilitate the incorporation of the halogen component and the uniform distribution of the metallic components throughout the carrier material. In addition, it is generally preferred to impregnate the carrier material after it has been calcined in order to minimize the risk of washing away the valuable platinum group compound.

After the platinum group component is combined with the porous carrier material the resulting platinum group metal containing carrier will generally be dried at a temperature of about 200° F. to about 600° F.

Such catalyst systems which are useful for the dehydrocyclization of paraffins can have additionally present therein, in addition to platinum, a rhenium component.

The overall techniques for the formation of various platinum group metal containing dehydrocyclization catalyst which are to be employed in the practice of the present invention are well known to those in the art and as such the preparation of suitable catalyst systems for use in the practice of the present invention do not form a part of the inventive concept of the present invention.

According to the present invention, the dehydrocyclizable hydrocarbon is contacted with the selected catalyst in a dehydrocyclization zone maintained at dehydrocyclization conditions. This contacting may be accomplished by using the catalyst in a fixed bed system, a moving bed system, a fluidized bed system or a dense-phase moving bed system. In a fixed bed system the dehydrocyclization feed stream is preheated by any suitable heating means to the desired reaction temperature and then passed into a dehydrocyclization zone containing a fixed bed of the selected dehydrocyclization catalyst. In the practice of the present invention the dehydrocyclization zone may be one or more separate reactors with suitable means therebetween to ensure that the desired conversion temperature is maintained at the entrance to each reactor.

The reactants may be controlled within the catalyst bed in either upward, downward or radial flow fashion. In addition, the reactant may be in the liquid phase, a mixed liquid-vapor phase or a vapor phase when they contact the catalyst, with best results obtained in the vapor phase.

Although hydrogen is the preferred diluent for use in the subject dehydrocyclization process, other art recognized diluents may be utilized either individually or in admixture with hydrogen, such as $C_1$ to $C_5$ paraffins. Hydrogen is preferred because it serves the dual function of not only lowering the partial pressure of the dehydrocyclizable hydrocarbon but also suppressing the formation of hydrogen deficient carbonaceous deposits (coke) on the catalyst composite.

It is generally preferred to carry out the dehydrocyclization process in a substantially water-free environment. To achieve this condition in the dehydrocyclization zone, the water level in the charge stock and the diluent stream which is being charged to the zone is controlled. Best results are obtained when the total amount of water entering the conversion zone from any source is held to a level less than 50 ppm. The charge stock can be dried by using any suitable drying means known to the art, such as a conventional solid adsorbent having a high selectivity for water such as silica gel and the like.

The hydrocarbon dehydrocyclization conditions used in the practice of the present invention include a reactor pressure which is selected from the range of about 0 psig to about 500 psig.

The temperature required for dehydrocyclization is generally in the range of about 800° F. to about 1100° F. It is well known to those skilled in the dehydrocyclization art that the initial selection of the temperature within this range is made primarily as a function of the desired conversion level of the dehydrocyclizable hydrocarbon considering the characteristics of the charge stock and the catalyst. Ordinarily, the temperature is thereafter slowly increased during the run to compensate for the inevitable deactivation that occurs to provide a relatively constant value for conversion.

The liquid-volume hourly space velocity (LHSV) used in the instant dehydrocyclization process is selected from the range of about 0.1 to about 100 $hr^{-1}$.

The term "liquid-volume hourly space velocity" as used herein, shall mean the numerical ratio of the rate at which at least one feed hydrocarbon is charged to the dehydrocyclization zone in liters per hour divided by the liters of catalyst contained in the dehydrocyclization zone to which the feed hydrocarbon is charged. The preferred LHSV of the feed hydrocarbon to the reaction zone can be in the range of from about 0.25 $hr^{-1}$ to about 25 $hr^{-1}$.

Generally the hydrogen is charged to the dehydrocyclization zone so as to provide a molar ratio of hydrogen to feed hydrocarbon in the range of about 0.01:1 to about 20:1. Preferably the ratio is in the range of about 0.1:1 to about 6:1.

The dehydrocyclization product, i.e., the effluent exiting the dehydrocyclization zone, can be subjected to any suitable separation means (e.g., fractional distillation) to separate the desired formed product hydrocarbon aromatics such as benzene, toluene and xylene which may be present in the product.

In the process of this invention, impurities can also be present in the dehydrocyclization feed stream. The impurities can include, but are not limited to, sulfur compounds, water, carbon dioxide, carbon monoxide, monocyclic aromatic hydrocarbons, olefins containing 2 to about 10 carbon atoms, as well as combinations thereof. The amounts of these additional impurities should be small enough that the impurities do not have a detrimental effect on the process of this invention. Generally, the total content of these impurities, if present, in the dehydrocyclization feed stream (on an elemental basis, based on the weight of at least one feed hydrocarbon) is in the range of about 1 ppm impurity to about 2,000 ppm impurity (i.e., about 1 to about 2,000 parts by weight of impurity per million parts by weight of at least one feed hydrocarbon). In most cases, the impurity content is in the range of from about 10 ppm to about 200 ppm.

The amount of water in the dehydrocyclization feed stream is either essentially zero or is not to exceed about 1 ppm $H_2O$ (i.e. about 1 part by weight of $H_2O$ per million parts by weight of at least one feed hydrocarbon). Thus, the dehydrocyclization feed stream should be dried (such as by employing an effective desiccant, such as, but not limited to, silica gel, calcium chloride, alumina, molecular sieves and the like as well as mixtures thereof) so as to reduce the water content of the dehydrocyclization feed stream to about 1 ppm $H_2O$, or less, preferably to about 0.2 ppm $H_2O$ or less. It is also necessary to use sufficiently dry hydrogen which can be mixed with the dehydrocyclization feed stream and to employ, if necessary, a desiccant (as described above) to dry the hydrogen, so as to ensure that the dehydrocyclization feed stream does not contain more than about 0.2 ppm $H_2O$ (based on the weight of the feed hydrocarbon portion of the dehydrocyclization feed stream).

The catalyst deactivating effect is counteracted in accordance with the process of this invention by the presence in the dehydrocyclization feed stream of an additive comprising a metal halide compound, preferably such metal halide compound is a metal chloride compound. The presence of the additive in the dehydrocyclization feed stream can be accomplished by adding the additive to the feed containing the dehydrocyclizable hydrocarbon and hydrogen in an amount sufficient to effect the counteracting of the deactivation of the dehydrocyclization catalyst used in the dehydrocyclization process. It is also feasible to inject the additive into the feed hydrocarbon stream or into the hydrogen stream. Since both the feed hydrocarbon stream and hydrogen stream are preferably mixed to form the dehydrocyclization feed stream, before their contact with the catalyst, the end result will be essentially the same as injecting the additive into the dehydrocyclization feed stream (containing at least one paraffinic hydrocarbon and hydrogen).

Examples of suitable metal chloride compounds include, but are not limited to, aluminum chloride, antimony trichloride, antimony pentachloride, boron chloride, and phosphorochloride as well as mixtures thereof.

In one presently preferred embodiment of this invention the metal chloride compound is aluminum chloride.

Generally, the effective amount of additive, preferably aluminum chloride ($AlCl_3$) in the dehydrocyclization feed stream is in the range of from about 0.01 ppb to about 10 ppb (i.e., about 0.01 part by weight additive per billion parts by weight of at least one feed hydrocarbon to about 10 parts by weight additive per billion parts by weight of at least one feed hydrocarbon).

An organic chloride compound and/or hydrogen chloride (such hydrogen chloride usually present as a result of the reaction of an organic chloride compound and hydrogen) may also be present in the dehydrocyclization feed stream of the inventive process. Examples of suitable organic chloride compounds include, but are not limited to, carbon tetrachloride, tetrachloroethylene, hexachloroethane, 1-chlorobutane, 1-chloro-2-methylpropane, 2-chloro-2-methylpropane and the like and mixtures thereof. The presently preferred organic chloride compound is tetrachloroethylene (also called perchloroethylene or PCE).

Through the use of the additive of the present invention there is achieved a prolonging of the catalyst life which in turn permits increased productivity prior to experiencing the need for catalyst regeneration. In addition, the BTX (benzene, toluene and xylene) production is also stabilized in contrast to the generally experienced erratic fluctuations in BTX yield. In addition, the octane number (RON) of the product is also stabilized and, contrary to the gradual decrease of RON with time on stream, there is achieved an increase of RON values for the product.

The following examples are presented to further illustrate the invention and are not to be considered as unduly limiting the scope of the invention. The following examples illustrate the unexpected performance of the inventive process which alleviates or diminishes the deactivation of a catalyst while simultaneously utilizing such catalyst in a dehydrocyclization of hydrocarbons.

In these examples, lab-scale tests are described to illustrate the process of this invention.

EXAMPLE I (Control)

A stainless-steel reactor having an inner diameter of about 0.75 inch and a height of about 28 inches was filled with a layer (about 13.5 inches high) of inert alumina particles having a surface area of 1 $m^2/g$ or less, a layer of about 6 inches of R-56 Pt/alumina reforming catalyst marketed by UOP, Des Plaines, Ill; containing about 0.25 weight percent platinum, about 0.40 weight percent rhenium, and about 1.0 weight percent Cl on gamma alumina, and a top layer of about 8 inches of inert alumina.

The catalyst system was activated at 940° F. by the introduction of hydrogen followed by addition of PCE at 32 microliters/hour for 15 minutes to give 0.2 weight percent chloride on the catalyst. Thereafter the system was purged with hydrogen for an additional 2 hours at 940° F.

While continuing the hydrogen flow at 900° F., a liquid naphtha feed having 18% n-paraffins, 28% isoparaffins, 9.9% aromatics and 44% naphthenes was introduced into the reactor at a liquid-volume hourly space velocity of about 2.5 $hr^{-1}$. The reaction pressure was about 300 psig. The liquid naphtha feed had an initial boiling point of 177° F. and an end point of 258° F. and an average molecular weight of 99.8.

The liquid naphtha feed was added in an amount such that the hydrogen:hydrocarbon ratio was 3.2.

To this system was then added PCE in an amount of 1.3 ppm to the hydrocarbon feed.

After 24 hours of operation, the following results of liquid product were obtained:

| | |
|---|---|
| Octane, RON | 88.3 |
| Liquid Volume of Feed to $C_5^+$ product | 70.72% |
| Benzene | 1.88% |
| Toluene | 43.1% |
| Xylene | 6.38% |

After 216 hours of operation, the following results were obtained:

| | |
|---|---|
| Octane, RON | 84.76 |
| Liquid Volume of Feed to $C_5^+$ product | 74.54% |
| Benzene | 1.92% |
| Toluene | 42.88% |
| Xylene | 4.99% |

EXAMPLE II (Invention)

To test the inventive process, a further run was carried out in the same manner as that above described in Example I with the exception that there was added to the liquid naphtha feed stream 0.16 ppb (parts per billion parts of feed) of aluminum chloride ($AlCl_3$).

After 24 hours of operation, the following results were obtained:

| | |
|---|---|
| Octane, RON | 88.39 |
| Liquid Volume of Feed to $C_5^+$ product | 76.07% |
| Benzene | 2.2% |
| Toluene | 45.30% |
| Xylene | 7.03% |

After 216 hours of operation, the following results were obtained:

| | |
|---|---|
| Octane, RON | 88.3 |
| Liquid Volume of Feed to $C_5^+$ product | 76.75% |
| Benzene | 2.11% |
| Toluene | 45.03% |
| Xylene | 7.09% |

The above data show that through the addition of low levels of aluminum chloride to the system in accordance with the present invention there is maintained the octane value of desired product while effecting a BTX increase.

EXAMPLE III (Control)

A stainless-steel reactor having an inner diameter of about 0.75 inch and a height of about 28 inches was filled with a layer about 13.5 inches high of inert alumina particles having a surface area of 1 m²/g or less, a layer of about 6 inches of R-56 Pt/alumina reforming catalyst marketed by UOP, Des Plaines, Ill; containing about 0.25 weight percent platinum, about 0.40 weight percent rhenium, and about 1.0 weight percent Cl on gamma alumina, and a top layer of about 8 inches of inert alumina.

The catalyst system was activated at 940° F. by the introduction of hydrogen followed by addition of PCE at 32 microliters/hour for 15 minutes to give 0.2 weight percent chloride on the catalyst. Thereafter, the system was purged with hydrogen for an additional 2 hours at 940° F.

While continuing the hydrogen flow at 900° F., a liquid naphtha feed having 19.3% n-paraffins, 30.6% isoparaffins, 25.7% aromatics, 23.5% naphthenes and 1.2% olefins was introduced into the reactor at a liquid-volume hourly space velocity of about 2.5 hr$^{-1}$. The reaction pressure was about 300 psig. The liquid naphtha feed had an initial boiling point of 176° F. and an end point of 385° F., an average molecular weight of 113, and an octane value of 67.50.

The liquid naphtha feed was added in an amount such that the hydrogen:hydrocarbon ratio was 3.2.

To this system was then added PCE in an amount of 1.3 ppm to the hydrocarbon feed.

After 24 hours of operation, the following results were obtained:

| | |
|---|---|
| Octane, RON | 94.60 |
| Liquid Volume of Feed to $C_5^+$ product | 79.09% |

After 120 hours of operation, the following results were obtained:

| | |
|---|---|
| Octane, RON | 93.20 |
| Liquid Volume of Feed to $C_5^+$ product | 83.30% |

EXAMPLE IV (Invention)

To test the inventive process, a further run was carried out in the same manner as that described above in Example III with the exception that there was added to the liquid naphtha feed stream 0.16 ppb (parts per billion parts of feed) of aluminum chloride ($AlCl_3$).

After 24 hours of operation, the following results were obtained:

| | |
|---|---|
| Octane, RON | 94.95 |
| Liquid Volume of Feed to $C_5^+$ product | 77.16% |

After 120 hours of operation, the following results were obtained:

| | |
|---|---|
| Octane, RON | 95.24 |
| Liquid Volume of Feed to $C_5^+$ product | 83.44% |

The above data show that through the addition of low levels of aluminum chloride to the system in accordance with the present invention there is maintained the high octane value of desired product to provide long term production of high octane product.

The results shown in the above examples clearly demonstrate that the present invention is well adapted to carry out the objects and attain the ends and advantages mentioned as well as those inherent therein.

Reasonable variations, modifications and adaptations for various conditions and reactants can be made within the scope of the disclosure and the appended claims without departing from the scope of the invention.

That which is claimed is:

1. In a process for the dehydrocyclization of a dehydrocyclizable hydrocarbon in a dehydrocyclization feed stream which comprises contacting said dehydrocyclizable hydrocarbon in a dehydrocyclization zone under dehydrocyclization conditions in the presence of a platinum group metal containing dehydrocyclization catalyst, the improvement comprises carrying out said dehydrocyclization process in the presence of aluminum chloride in said dehydrocyclization feed stream, said aluminum chloride being present in an amount in the range of about 0.01 to about 10.0 ppb.

2. A process according to claim 1 wherein said dehydrocyclizable hydrocarbon is an aliphatic hydrocarbon containing 6 to 20 carbon atoms.

3. A process according to claim 2 wherein said aliphatic hydrocarbon contains from 6 to 10 carbon atoms.

4. A process according to claim 2 wherein said aliphatic hydrocarbon is n-heptane.

5. A process according to claim 2 wherein said aliphatic hydrocarbon has been dried prior to introduction into said dehydrocyclization zone.

6. A process according to claim 1 wherein said dehydrocyclization catalyst is a platinum group compound on a porous carrier.

7. A process according to claim 6 wherein said porous carrier is a refractory inorganic oxide.

8. A process according to claim 7 wherein said refractory inorganic oxide is alumina.

9. A process according to claim 1 wherein said dehydrocyclization feed stream is a naphtha fraction boiling in the range of about 122° F. to about 450° F.

10. A process according to claim 9 wherein said naphtha fraction is one boiling in the range of about 150° F. to about 400° F.

11. A process according to claim 1 wherein said dehydrocyclization conditions include a temperature in the range of about 800° F. to about 1100° F., a pressure in the range of about 0 to about 500 psig and a LHSV of about 0.1 to about 100 hr$^{-1}$.

12. A process according to claim 1 wherein the contacting is performed in a substantially water-free environment.

* * * * *